United States Patent [19]

Heim et al.

[11] Patent Number: 4,798,689

[45] Date of Patent: Jan. 17, 1989

[54] ARRANGEMENT FOR CONTROLLING A VAPORIZER BY MEANS OF PRESSURE FLUCTUATIONS

[75] Inventors: Ulrich Heim, Lübeck; Scato Albarda, Gross Schenkenberg, both of Fed. Rep. of Germany

[73] Assignee: Drägerwerk Aktiengesellschaft, Lübeck, Fed. Rep. of Germany

[21] Appl. No.: 147,449

[22] Filed: Jan. 25, 1988

[30] Foreign Application Priority Data

Jan. 24, 1987 [DE] Fed. Rep. of Germany ....... 3702136

[51] Int. Cl.⁴ .......................................... A61M 16/18
[52] U.S. Cl. .................................... 261/39.1; 261/52; 261/96; 261/DIG. 65; 261/DIG. 74; 128/203.14; 128/203.25; 128/204.13; 137/625.5
[58] Field of Search .......... 261/39.1, 52, 96, DIG. 65, 261/DIG. 74; 128/203.14, 203.25, 204.13; 137/625.5

[56] References Cited

U.S. PATENT DOCUMENTS

| | | | |
|---|---|---|---|
| 3,298,674 | 1/1967 | Gilbertson | 261/52 |
| 3,752,452 | 8/1973 | Iannelli | 261/52 |
| 3,841,560 | 10/1974 | Sielaff | 128/203.25 |
| 3,923,934 | 12/1975 | Watkins | 261/52 |
| 4,017,566 | 4/1977 | Seidel | 261/39.1 |
| 4,129,621 | 12/1978 | Jones et al. | 128/203.25 |
| 4,345,612 | 8/1982 | Koni et al. | 128/203.25 |

Primary Examiner—Tim Miles
Attorney, Agent, or Firm—Walter Ottesen

[57] ABSTRACT

The invention is directed to an arrangement for generating a gas mixture. The arrangement includes a vaporizer which is switched into a vaporizer line which starts at a supply line and opens into a user line with the vaporizer line being bridged by a bypass line. The influence of material parameters associated with the metering of the vaporized gas quantity is reduced. For this purpose, the vaporizer line is alternately interrupted at the input and the output of the vaporizer and, when interrupted at the output side, the user line is interrupted by means of a switching element arranged therein.

5 Claims, 2 Drawing Sheets

ARRANGEMENT FOR CONTROLLING A VAPORIZER BY MEANS OF PRESSURE FLUCTUATIONS

FIELD OF THE INVENTION

The invention relates to an arrangement for generating a gas mixture wherein a vaporizer is switched into a vaporizer line. The vaporizer line extends from a supply line and opens into a user line with the vaporizer line being bridged by means of a bypass line.

BACKGROUND OF THE INVENTION

A vaporizer of the above type is disclosed in U.S. Pat No. 4,017,566. The vaporizer vaporizes a liquid anesthetic which is contained in an appropriate vessel through which a component flow of a carrier gas is conducted. The carrier gas can, for example, be oxygen which is saturated with the anesthetic vaporized via a wick. The component flow of the carrier gas which is free of anesthetic is again conducted to the component flow containing anesthetic via a bypass line connected in parallel to the input and the output of the vaporizer. This gas mixture is conducted to a user for breathing who in the familiar situation is a patient. The concentration of the gas mixture which is formed is determined by means of the adjustable proportion of the through-flow of the vaporizer and the bypass line.

The vaporized quantity of a liquid is dependent from several parameters such as the temperature of the liquid. For this reason, an appropriate arrangement is provided for the known vaporizer for compensating for this temperature influence on the vaporized quantity. Other external parameters not influenceable by the user of the vaporizer, however, as before, lead to undesired fluctuations of the quantity of vapor given off.

The adjustment of the component flows through the vaporizer and through the bypass line are adjusted in the known vaporizer by means of an adjustable flow resistance which is dependent upon the flow velocity. In addition, fluctuations in pressure at the output of the vaporizer can lead to flow fluctuations in the vaporizer itself and thereby lead to fluctuations in the vaporization quantity delivered to the carrier gas. Also, when there are changes in the type of carrier gas, the flow relationships in the flow resistances change and lead to a varying division of the component flows through the vaporizer and through the bypass line.

Since a large range of application of the known vaporizer for vaporizing volatile anesthetic mediums with a high partial pressure serves for assisted or mandatory ventilation of anesthetized patients and because a most precise and fluctuation-free metering of the anesthetic is required for this application, the above-mentioned external influences on the vaporizer are considerable and lead to undesired fluctuations in the concentration of the anesthetic in the carrier gas.

SUMMARY OF THE INVENTION

It is therefore an object of the invention to provide an arrangement of the above-mentioned type which is improved so that the influence of parameters specific to a particular gas on the vaporized quantity is reduced.

According to a feature of the invention, the vaporizer line is alternately interrupted at the input and the output of the vaporizer and, when the vaporizer line is interrupted at the output, the user line is interrupted by means of a switching element arranged in the latter.

An advantage of the invention is that a charging of the vaporizer with the carrier gas occurs by means of a wanted increase in pressure and, that the concentration of a gas mixture can be varied by controlling the vaporized gas component given off to the carrier gas. In this situation, the parameters dependent upon flow and the specific type of gas have no influence.

If the vaporizer line at the output thereof is interrupted while simultaneously the user line, too, is interrupted, the bypass flow and the carrier gas flow are simultaneously interrupted with the input of the vaporizer to the supply line however remaining connected. In this way, a pressure of the carrier gas builds up within the vaporizer which is determined by the pumping means generating the carrier gas flow such as a pneumatically or electrically operated metering unit or pump. This charging period is ended in that the vaporizer is simultaneously connected at its output with the bypass line as well as with the user line and is separated at its input end from the supply line. Now, the carrier gas can flow to the user through the bypass line with the vaporization quantity being supplied in the direction of the user line because of reducing pressure.

By alternately connecting the vaporizer input and output, a pulse-like charging of the vaporizer with carrier gas is achieved with the carrier gas being enriched with anesthetic and which is compelled to escape from the vaporizer only in the direction of the user line. A back and forth flow of the carrier gas through the vaporizer is thereby prevented.

The pressures required for charging the vaporizer volume are very low in comparison to the pressures which are necessary for generating the carrier gas flow. For this reason, a sufficiently high pressure is always built up when the vaporizer is blocked from the user line and the bypass line so that an adequate quantity of gaseous vaporization medium can be formed.

A defined quantity of saturated carrier gas is conducted into the user line with each cycle of interruption and connection of the vaporizer to the carrier gas flow. This defined quantity can be varied by selecting the connecting and interrupting times.

The interruption of the carrier gas flow can be performed in a simple manner by means of a driveable input valve at the input of the vaporizer and by a driveable output valve at the output of the vaporizer. A blocking valve interrupts the user line with the output of the vaporizer being simultaneously separated from the bypass line and the user line by means of the output valve. If the blocking valve and the output valve are opened and the input valve is closed, then the carrier gas enriched with vaporized medium can flow from the bypass line and be conducted through the user line to the user with a return flow from the vaporizer into its input line being prevented by means of the closed input valve.

The concentration of the gas mixture in the user line is determined by the opening duration of the blocking valve in that the gas quantity provided from the vaporizer chamber is diluted with a predetermined quantity of carrier gas in the user line. The control of the valves can be achieved either by means of pulse-width modulation or pulse-frequency modulation. Typical values for a complete switching cycle for the above are approximately 50 ms with the time for charging the vaporizer with the carrier gas pressure being about 1 ms.

Even if the pressure fluctuations in the user line are low because of the favorable pulse-width ratio, it can be advantageous to provide a buffer chamber in the user line downstream of the blocking valve for further smoothing pressure fluctuations and for compensating for jumps in concentration of vaporization medium in the carrier gas.

The arrangement according to the invention is especially suitable in combination with a precise metering unit to introduce the vaporization medium into the carrier gas flow in smallest quantities and such that they are reproducible.

According to another feature of the invention, a compact structure is achieved by combining the input valve and the output valve arranged in the vaporizer line into a single magnetic valve having two seats opening into a valve chamber through which carrier gas can flow and by leading the bypass line diametrically through this valve chamber. The seats form the ends of the vaporizer line. With this combined configuration, not only is a very compact construction achieved; instead, and most importantly, any dead space between the valve seat and the bypass line is prevented which could lead to a falsification of the concentration of the gas mixture. By utilizing a ball as a closure body switchable between the two seats, a high switching frequency is realized.

BRIEF DESCRIPTION OF THE DRAWINGS

The invention will now be explained with reference to the drawings wherein.

DESCRIPTION OF THE PREFERRED EMBODIMENTS OF THE INVENTION

Figure 1:
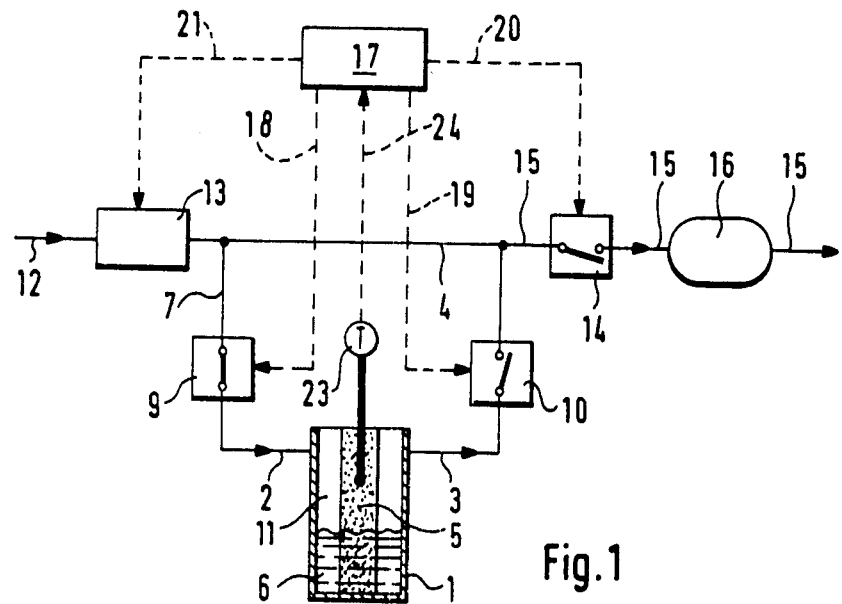
FIG. 1 is a block diagram showing a circuit arrangement of the vaporizer in accordance with one embodiment of the invention.

The vaporizer 1 shown in FIG. 1 is connected with its input 2 and its output 3 to a bypass line 4 via a vaporizer line 7. In the vaporizer 1, a wick 5 is dipped into a vaporization liquid 6 such as an anesthetic. The input 2 of the vaporizer 1 is connected to the output of a controllable input valve 9 and the output 3 of the vaporizer 1 is connected to a controllable output valve 10. The carrier gas can for example be oxygen and is conducted from a supply line 12 into a metering unit 13 and from there into the vaporizer line 7 and into the bypass line 4 as shown. The bypass line 4 continues into a user line 15 and this, in turn, leads to a user (not shown) via a blocking valve 14 and a buffer vessel 16. A control unit 17 controls the valves (9, 10, 14) via the corresponding control lines (18, 19, 20). In addition, the control unit 17 issues control commands via a metering control line 21 to the metering unit 13. A temperature sensor 23 in the vaporizer 1 transmits the corresponding temperature values to the control unit 17 via a temperature-signal line 24.

In the switching condition shown, the input valve 9 is opened and the output valve 10 and the blocking valve 14 are closed. As an example, it is assumed that the carrier gas is oxygen and that the vaporization liquid 6 is an anesthetic. Oxygen is conducted from the metering unit 13 into the vaporization chamber 11 of the vaporizer 1 and builds up pressure there. Anesthetic liquid vaporizes from the anesthetic 6 into the oxygen gas which is at a slight overpressure, that is maximally up to the saturation of the gas phase at the temperature which is present. The control unit 17 issues a control command to the valves (9, 10, 14) via the corresponding control lines (18, 19, 20). This control command is such that the input valve 9 is closed thereby interrupting the charging operation for generating an overpressure and such that simultaneously the output valve 10 and the blocking valve 14 are opened. In this way, the flow of carrier gas directly enters into the user line 15 via the bypass line 4. The user line 15 includes the blocking valve 14 and the buffer vessel 16. At the same time, the carrier gas enriched with the anesthetic flows out of the vaporizer 1 via the output valve 10 into the bypass line 4 to the user line 15 whereby the overpressure is reduced also in the vaporization chamber 11. In this way, the user (not shown) receives an oxygen gas mixture enriched with anesthetic. By varying the switching times of the blocking valve 14, the concentration of the anesthetic can be determined which should be fed to the user gas during a switching cycle.

Figure 2:
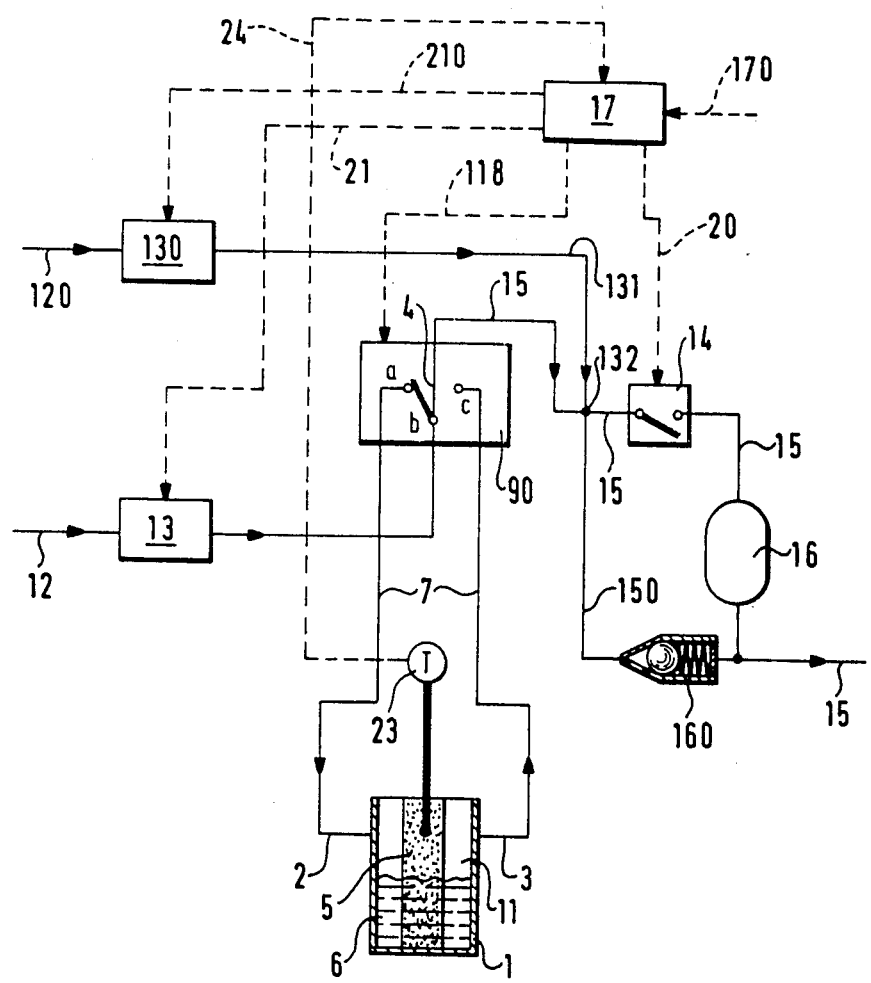
FIG. 2 is a block diagram showing another circuit arrangement of a vaporizer pursuant to a further embodiment of the invention; and, FIG. 3 is an elevation view, in section, taken through the magnetic ball valve according to a feature of the invention.

FIG. 2 illustrates another circuit arrangement for the vaporizer 1. The components shown in FIG. 2 which correspond to those in FIG. 1 are provided with the same reference numerals.

The carrier gas can, for example, again be oxygen and is conducted via a metering unit 13 to a switching valve 90. The switching valve 90 is configured as a throwover switch having two working positions and a continuous through-passage which serves as a bypass line. The center connection (b) is connected to the side connection (a) in the switching position shown by means of which the input 2 of the vaporizer 1 is connected to the carrier gas flow from the supply line 12. The output 3 of the vaporizer 1 is separated from the bypass line 4 via the closed side connection (c). The bypass line 4 is connected with the user line 15. An additional gas line 131 opens into the user line 15 at a junction point 132 which, on the one hand, is connected with the blocking valve 14 and, on the other hand, is connected via a bypass line 150 to an overpressure valve 160. In the switching position shown, the blocking valve 14 interrupts the user line 15.

A further supply line 120 is connected with the gas line 131 via an additional metering unit 130. With these components, a further gaseous anesthetic can, for example, be conducted to the junction point 132. The additional metering unit 130 is likewise connected to the control unit 17 via its control line 210. Desired value data is supplied to the control unit 17 via the input line 170. In correspondence to these desired value data, the control unit 17 triggers: the metering unit 13 via line 21, the throwover switch 90 via the throwover switch line 118 as well as the blocking valve 14 via the line 20.

In the switching position shown, the vaporization chamber 11 is charged with the carrier gas which can, for example, be oxygen. Also for the switching condition shown, the output 3 of the vaporizer 1 is separated from the bypass line 4 by the closed side connection (c) of the throwover switch 90 and the supply line 15 is interrupted because of the closed blocking valve 14.

The overpressure valve 160 in the bypass line 150 makes possible a reduction in pressure into the user line 15 and into the buffer vessel 16 when undesired high pressure is generated either in the bypass line 4 or in the gas line 131. Pursuant to commands from the control unit 17, the throwover switch 90 and the blocking valve 14 are brought into the second switching position (not shown) wherein the center connection (b) is connected with the side connection (c) and the blocking valve 14 is opened. The gas enriched with anesthetic can now flow from the vaporization chamber 11 into the bypass line 4 and the user line 15.

Figure 3:
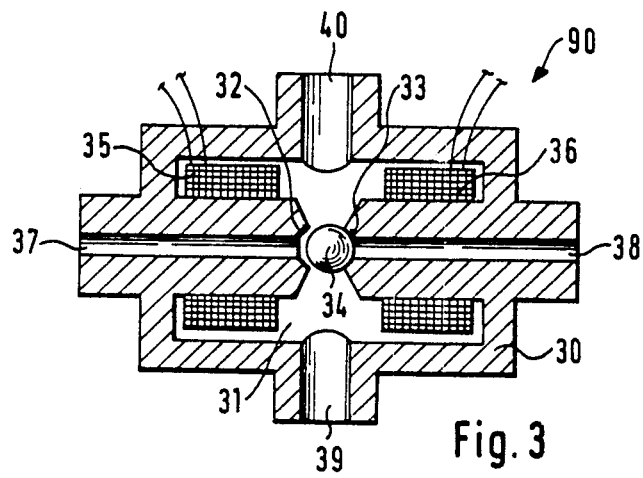

FIG. 3 shows the throwover switch 90 in the form of a magnetic valve and the circuit arrangement thereof is analogous to that shown schematically for the switch 90 in FIG. 2. A housing 30 defines a valve chamber 31 in the interior of the magnetic valve. The valve chamber 31 has two seats (32, 33) which lie opposite each other and between which a ball 34 can move. Each seat (32, 33) is surrounded by a corresponding one of the coils (35, 36). The channels (37, 38) lead to corresponding ones of the seats (32, 33). The channel 37 is connected to the input 2 of the vaporizer 1 and the channel 38 is connected with the output 3 of the vaporizer 1.

In a plane extending between the two seats (32, 33) and perpendicularly to the axis of these seats, the valve chamber 31 has two connecting terminals (39, 40) disposed opposite each other of which one connecting terminal 39 is connected with the supply line 12 and the other connecting terminal 40 is connected with the user line 15. The control unit 17 drives the coils (35, 36) so as to alternately excite the same. The ball 34 then moves toward the particular coil which is energized (for example coil 36) and closes the seat (for example seat 33 as shown) corresponding thereto; whereas, the other seat (for example seat 32) is then open. In this way, the valve chamber 31 defines the continuous connection between the supply line 12 and the user line 15 in the region of the seats and is connected with either the input 2 or output 3 of the vaporizer 1 in accordance with the switching position. The valve chamber 31 thereby corresponds to a bypass line 4 which is shortened to an outermost extent. For this reason, there are no dead spaces between the closure line of the ball 34 against the seat (32 or 33) and the bypass line formed in this manner.

It is understood that the foregoing description is that of the preferred embodiments of the invention and that various changes and modifications may be made thereto without departing from the spirit and scope of the invention as defined in the appended claims.

What is claimed is:

1. An arrangement for generating a gas mixture, the arrangement comprising:
   supply means for supplying a carrier gas;
   a user supply line for conducting a gas mixture to a user;
   a vaporizer line starting at said supply means and opening into said user supply line;
   a vaporizer for vaporizing a medium, said vaporizer having an input and an output for connecting said vaporizer into said vaporizer line;
   a bypass line bridging said vaporizer line and connecting said supply means to said supply line;
   primary switching means for alternately interrupting said vaporizer line at said input and at said output; and,
   ancillary switch means for interrupting said user supply line when said vaporizer line is interrupted at said output.

2. An arrangement for generating a gas mixture, the arrangement comprising:
   supply means for supplying a carrier gas;
   a user supply line for conducting a gas mixture to a user;
   a vaporizer line for conducting a component of said carrier gas away from said supply means, said vaporizer line starting at said supply means and opening into said user supply line;
   a vaporizer for vaporizing a medium, said vaporizer having an input and an output for connecting said vaporizer into said vaporizer line;
   a bypass line bridging said vaporizer line and connecting said supply means to said user supply line for conducting carrier gas to the latter;
   an input valve connected to said input and being switchable between first and second positions for respectively passing and interrupting the flow of said component into said vaporizer wherein said component causes fluctuations in pressure and the vaporized medium becomes entrained in the carrier gas passed therein to form a gas mixture;
   an output valve connected to said output and being switchable between first and second positions for respectively passing and interrupting the flow of said gas mixture to said user supply line;
   a blocking valve mounted in said user supply line and being switchable between first and second positions for respectively passing and blocking the flow of the gas mixture to the user; and,
   control means for driving said input valve, said output valve and said blocking valve alternately between two modes of operation, the one mode causing said input valve to switch into said first position while at the same time causing said output valve and said blocking valve to switch into said second position thereby interrupting the flow of said gas mixture to the user; and, the other mode causing said valves to be driven so as to switch said input valve into said second position while switching said output valve and said blocking valve into said first position for passing said gas mixture into said user supply line and to the user.

3. The arrangement of claim 2, further comprising: buffer chamber means disposed in said user supply line downstream of said blocking valve for smoothing pressure fluctuations in said gas mixture supplied to the user.

4. The arrangement of claim 2, said supply means comprising a metering unit connected to said bypass line and said vaporizer line for metering the carrier gas into said lines.

5. The arrangement of claim 2, wherein said input valve and said output valve conjointly define a single magnetic valve unit, said valve unit comprising:
   a housing defining a valve chamber;
   inlet valve seat means formed in said housing and being connected to said input of said vaporizer and opening into said valve chamber;
   outlet valve seat means formed in said housing and being connected to said output of said vaporizer and likewise opening into said valve chamber;
   a first terminal connection opening into said valve chamber and connected to said supply means for conducting said carrier gas into said chamber and a second terminal connection likewise opening into said valve chamber and connected to said user supply line for passing said gas mixture into the latter; and,
   electromagnetic actuation means connected to said control means for alternately closing and opening said valve seats in said two modes of operation.

* * * * *